United States Patent [19]

Comben et al.

[11] 3,957,056

[45] May 18, 1976

[54] POWER-SOURCE CANISTER

[75] Inventors: Richard H. Comben, Minneapolis; Richard L. Doty, White Bear Lake, both of Minn.

[73] Assignee: Medtronic, Inc., Minneapolis, Minn.

[22] Filed: Nov. 25, 1974

[21] Appl. No.: 526,590

[52] U.S. Cl............................ 128/419 R; 128/419 P; 136/166; 220/83
[51] Int. Cl.²......................................... A61N 1/36
[58] Field of Search ............ 128/1 R, 419 B, 419 C, 128/419 E, 419 P, 419 PG, 419 PS, 419 R, 421, 422; 136/168, 166; 220/83, 3.8

[56] References Cited
UNITED STATES PATENTS

| | | | |
|---|---|---|---|
| 2,987,909 | 6/1961 | Shlank | 220/3.8 |
| 3,649,367 | 3/1972 | Purdy | 128/419 pS |
| 3,735,766 | 5/1973 | Bowers et al. | 128/419 P |
| 3,818,304 | 6/1974 | Hursen et al. | 128/419 PS |
| 3,822,707 | 7/1974 | Adducci et al. | 128/419 PS |
| 3,823,037 | 7/1974 | Cairns et al. | 136/166 |

*Primary Examiner*—William E. Kamm
*Attorney, Agent, or Firm*—Wayne A. Sivertson; Lew Schwartz

[57] ABSTRACT

An improved power-source canister for isolating a power source from the device or devices to be powered when packaged therewith for implantation in a living animal body. The canister is formed by a bottom wall and a continuous side wall and is provided with a cover. Feed-through terminals pass through the side wall, at locations spaced along the perimeter of the side wall, for making an electrical connection between a power source within the canister and the device or devices to be powered. The side wall is formed by four generally straight portions of approximately equal length, each straight portion being generally perpendicular to two of the others and generally parallel to a third. The straight portions are joined by arcuate portions having a radius of curvature approximately equal to one-fourth the distance between parallel straight portions. In a preferred embodiment, the side wall is provided with a flange and the cover is coextensive with the flange such that the cover may be secured to the canister and seal its inner void by means of a heat generating sealing process applied at a point spaced from the canister inner void. The side wall may also include a bevelled portion through which the feed-through terminals extend, and in another preferred embodiment, the flange and cover may be provided with a portion which is arcuate in cross section with the inclination of the feed-through terminals resulting from their passage through the bevelled portion of the side wall serving to reduce interference between the feed-through terminals and the arcuate portion of the flange during the process of making an electrical connection to the feed-through terminals.

37 Claims, 5 Drawing Figures

POWER-SOURCE CANISTER

BACKGROUND OF THE INVENTION

Typical implanatable cardiac pacemakers include a self-contained power source. The time between implant and explant of such pacemakers is most commonly determined by the power-source life and, to maximize the like of the implanted pacemaker, a great portion of the overall pacemaker volume has been devoted to the power source.

Obviously, pacemaker life can be increased by increasing the size of the power source. However, in most instances this would require an increase in the size of the pacemaker which is contrary to the general pacemaker design criterion that the pacemaker be as small as possible. Thus, typical prior art implantable cardiac pacemakers have sacrificed pacemaker life in favor of pacemaker size in an optimization of those factors.

There has been an ongoing effort to increase pacemaker life and/or to reduce the pacemaker size through the improvement of power-source power density (the ratio of available power and volume) as well as the power-source life itself. Recent developments have seen improvement of the power-source systems commonly used to power cardiac pacemakers, such as a zinc-mercury system, for example, as well as the development of new power-source systems, one example of which is a lithium-iodide system. These differing power-source systems, while offering the advantage of increased pacemaker life and the possibility of a decrease in pacemaker size, have differing physical characteristics which heretofore has required independent design of the pacemaker unit to optimally incorporate the power source within the pacemaker package. That is, the power-source systems presently and soon to be available for use within a pacemaker come in a variety of sizes and shapes having circular, rectangular and square cross sections, for example. Additionally, some of the power-source systems must be hermetically sealed to isolate them from the remainder of the pacemaker unit while others need not be isolated in any manner.

There is no efficient system known to the prior art whereby the many sizes and shapes pacemaker power sources may be accommodated within a single pacemaker design, particularly in those instances where the power source must be isolated from the remainder of the pacemaker unit.

SUMMARY OF THE PRESENT INVENTION

The present invention provides a power-source canister which can be easily incorporated into existing pacemaker designs. Generally speaking, a pacemaker unit should be as small as possible or, alternatively, of a shape which will be perceived as small by the biological environment. Since most pacemakers are implanted near the surface of the skin, a relatively flat shape is often selected. Within this constraint, the surface area to volume ratio is optimized in a squat cylinder. This shape is a beginning point for many pacemaker designs with the edges of the cylinder being tapered to reduce the perception of thickness by the body. Thus, the layer pacemaker components are commonly located within the central area which is the position where the pacemaker thickness is the greatest.

The power-source canister of the present invention is adapted to be incorporated within a pacemaker unit configured as described above. Of course, it may be modified in obvious manner, to be located outside the central region of the pacemaker, where appropriate. The canister is formed by a bottom wall and a continuous side wall and is provided with a cover. The side wall is formed by four generally straight portions of approximately equal length, each straight portion being generally perpendicular to two of the others and generally parallel to a third. The straight portions are joined by arcuate portions having a radius of curvature approximately equal to one-fourth the distance between the parallel straight portions. A canister configured in this manner can accept at least four disc-shaped batteries having a radius equal to or less than the radius of curvature of the arcuate portions which join the straight portions of the continuous side wall. Alternatively, batteries having square or rectangular cross sections can be easily accommodated within the canister in obvious manner. Thus, the unique shape of the canister of the present invention can easily accommodate the presently available and contemplated pacemaker power sources without regard to their configuration.

The side wall of the canister is provided with a flange and the cover is coextensive with the flange. The terminating edges of the flange and cover provide a means for securing the cover to the canister and hermetically sealing the internal volume of the canister, where appropriate, without encroachment on the internal void of the canister. Additionally, the flange and cover combination allow the use of a heat generating sealing operation, such as welding, at a point spaced from the internal void of the canister which reduces the effects of heat on the power sources within the canister. In a preferred embodiment, feed-through terminals are provided within the side wall of the canister and are spaced from each other along the perimeter of the side wall so that no terminal blocks access to another. In this manner, power sources within the canister are easily connected to the terminals and that connection is not disturbed by placement or removal of the cover. The terminals may be positioned in a bevelled portion of the side wall, which extends from the side wall to the flange, to facilitate exposure of the terminals within the canister inner void or cavity. In some instances, it may be necessary to provide the flange and cover with an arcuate portion such that the canister can be easily accommodated within a pacemaker unit of the type having tapered edges. In such cases, the inclination of the terminals resulting from their passage through the bevelled portion of the side walls will reduce the interference of the arcuate portion of the flange when making a connection between the devices to be powered and the terminals.

The many objects, advantages and novel features of the present invention will become apparent from a consideration of the following detailed description of the preferred embodiments when considered in conjunction with the drawings.

DETAILED DESCRIPTION OF THE DRAWINGS

Figure 1:
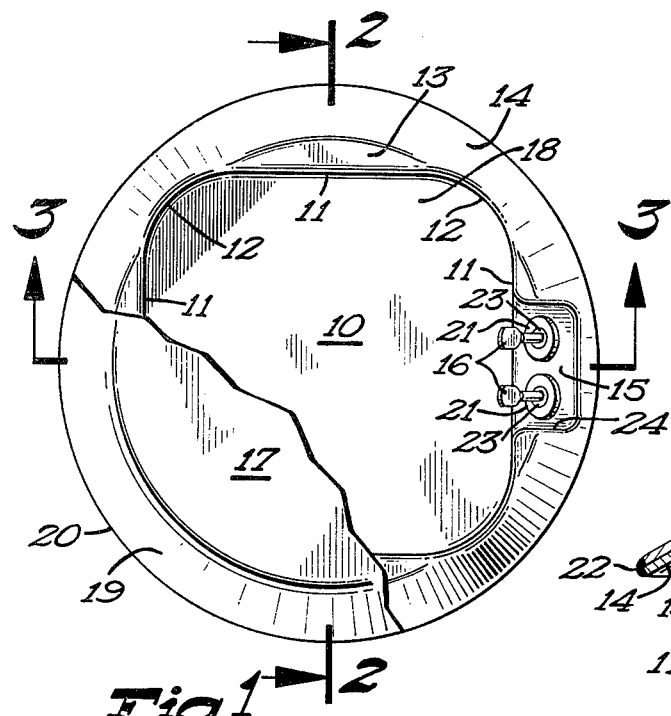
FIG. 1 is a partial cutaway of a top view of a preferred embodiment of the present invention.

FIG. 1 illustrates a preferred embodiment of the power-source canister of the present invention in which the canister inner void or cavity is defined by a bottom wall 10 and a side wall composed of four generally straight portions 11 joined to each other by arcuate side wall portions 12. As illustrated, the straight portions are of approximately equal length, each being generally perpendicular to two of the others and generally parallel to a third. For reasons to be explained more fully below, the arcuate side wall portions 12 have a radius of curvature approximately equal to one-fourth the distance between the parallel ones of the straight side wall portions 11. A flange 13 having an arcuate flange portion 14 extends from the side wall and a bevelled portion 15 extends from a straight portion 11 of the side wall to the flange 13. Walls 24 extend between the bevelled portion 16 and the side wall and feed-through terminals 16 pass through the bevelled portion 15. A cover 17 overlies the canister cavity.

Figure 2:
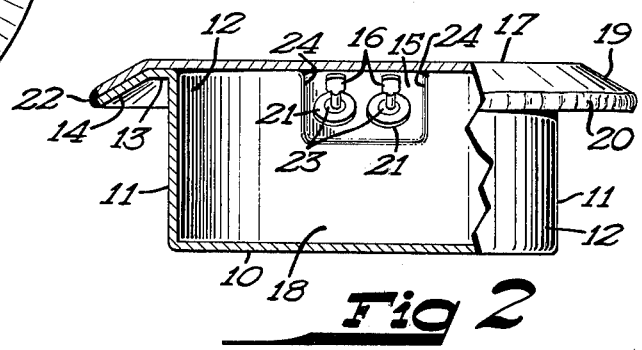
FIG. 2 is a partial cross section taken along the line 2—2 in Figure.

Referring now to FIG. 2, there is shown a partial cross section of the preferred embodiment of FIG. 1 taken along the line 2—2 in FIG. 1. As seen in FIG. 2, the inner void or cavity 18 of the canister of the present invention is defined by the bottom wall 10 and the continuous side wall formed by the straight portions 11 and arcuate portions 12. The flange 13 extends from the side wall and terminates at the arcuate flange portion 14. The cover 17 is coextensive with the flange and includes an arcuate cover portion 19 which is complementary to the arcuate flange portion 14. With the cover 17 in position on the canister of the present invention, the canister inner void or cavity 18 is closed and the cover 17 may be secured over the cavity 18 through the flange 13 without encorachment on the cavity 18. Such attachment may be by any means known to the prior art such as bonding with any suitable adhesive. However, in those applications where the power sources to be positioned within the cavity 18 must be isolated from the device or devices to be powered, when a corrosive electrolyte such as lithium-iodide is used, for example, the cavity 18 may be hermetically sealed. A preferred manner of hermetically sealing the cavity 18 is through the use of a heat generating sealing process such as welding. The bead resulting from such a process is illustrated at 20 in FIG. 2. Thus, through the cooperation of the flange 13 and a cover 17 which is coextensive with the flange 13, the cavity 18 may be hermetically sealed through the use of a heat generating sealing process at a point spaced from the cavity to minimize the effects of heat on the power sources contained therein.

Figure 3:
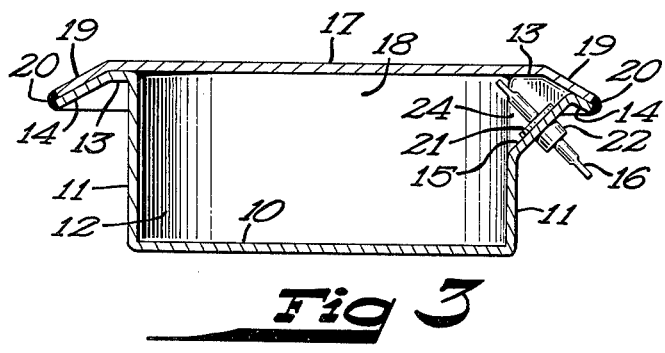
FIG. 3 is a cross section section taken along the line 3—3 in FIG. 1.

As described above, pacemakers are commonly cylindrically shaped with their sides tapering towards each other to reduce the perception of thickness by the body. The embodiment of FIGS. 1–3 is uniquely adapted to fit within such a system, particularly within the central region of the pacemaker unit. The overall height of the power-source canister is selected to accommodate the thickness of the power source or sources to be contained therein while still falling within the thickness of the pacemaker at its central portion. The arcuate portions 14 and 19 of the flange 13 and cover 17, respectively, are similarly intended to accommodate the tapering sides of the pacemaker unit while providing an extension away from the cavity 18 for the purpose of allowing the use of a heat-generating sealing process without effect on any power sources which might be housed within the cavity 18. The amount of curvature within the flange and cover is dependent upon the overall configuration of the pacemaker unit itself and is easily determinable for any such unit. It should be noted, that the central portion of the cover 17 need not be flat. Instead, it can be provided with a curvature, crown or other configuration which will accommodate itself in the overall design of the pacemaker unit. Of course, if the pacemaker design will permit, the entire cover 17 and flange 13 may be flat.

Referring now to FIG. 3, there is shown a cross section taken along the line 3—3 in FIG. 1. In FIG. 3, the cavity is again illustrated as being formed by the bottom wall 10 and the continuous side wall. The bevelled portion 15 extends between one of the straight portions 11 of the side wall to the flange 13. As illustrated, the bevelled portion 15 engages the arcuate flange portion 14. However, the point at which the bevelled portion 15 engages the flange is dependent upon the dimensions of the flange and the existence or non-existence of the arcuate flange portion 14, the particular configuration of the flange 13 at the point it is engaged by the bevelled portion 15 being non-critical in the present invention. Feed-through terminals 16 are supported through the bevelled portion 15 of the side wall by a collar 21 which engages the inner face of the bevelled portion 15 and has a tubular portion 22 of a smaller diameter extending through the bevelled portion 15. The collar 21 and portion 22 are insulated from the terminals 16 by an insulating member 23 (see FIG. 1) surrounding the terminal 16 and the entire assembly is spot welded to the bevelled portion 15. The assembly composed of the terminal 16, collar 21, portion 22 and insulation 23 are known to the art and form no part of the present invention beyond the combination with, and placement within, the power-source canister of the present invention.

By passing the feed-through terminals 16 through the canister side wall, the power sources may be positioned within the cavity 18, connected to the terminals 16, and that connection tested. The cover may then be positioned over the cavity 18 and secured and/or sealed, as desired, without disturbing the connection between the terminals 16 and the power source or power sources within the cavity 18. The cover may also be removed without disturbing the connection. The inclination of the terminals 16 resulting from their passage through the bevelled portion 15 of the side wall makes the terminals 16 easily accessible within the cavity 18 by inclining them toward the canister opening. The terminal inclination also reduces the terminal intrusion into that portion of the cavity 18 intended to be occupied by the power source or power sources. Additionally, it is part of the present invention to space each of the terminals 16 from the others along the perimeter of the side wall, whether through a bevelled portion 15, or otherwise, such that no terminal 16 obscures the view or access to the others within or without the cavity 18.

Figure 4:
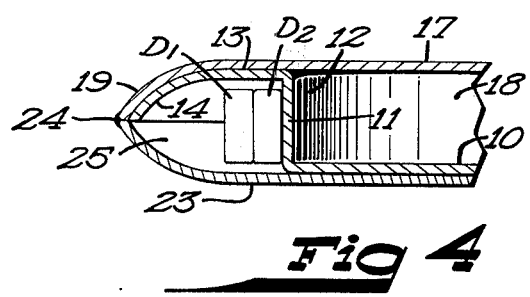
FIG. 4 illustrates a cross section of another preferred embodiment of the present invention.

Referring now to FIG. 4 there is shown, in cross section, a modification of the preferred embodiment of FIGS. 1–3 in which the power-source canister and cover form a part of the pacemaker body. The canister has a cavity 18 defined by the bottom wall 10 and continuous side wall 11. The flange 13 again extends from the side wall and terminates at an arcuate flange portion 14 with the cover 17 being provided with an arcuate cover portion 19 complementary to the arcuate portion 14 of the flange 13. In the embodiment of FIG. 4, the cover 17 and its arcuate portion 19 define one-half of the outer surface of the pacemaker unit. The other half is defined by a member 23 having a shape generally conforming to that of the cover 17 and its arcuate portion 19 which abuts against the terminus of the arcuate portion 19 of the cover 17. Thus, the cover 17 and member 23 define the pacemaker configuration and the flange 13, cover 17 and member 23 may be joined, for example by welding, at their junction 24 to seal the pacemaker unit as well as the canister. The space 25 without the cavity 17 defined by the flange 13, cover 17 and member 23 is intended to house the device or devices D1 and D2 making up the pacemaker circuitry, in known manner, which device or devices D1 and D2 are intended to be powered by the power sources within the cavity 18. The cover 17, member 23, or both, may be made of a conductive material and be suitably connected to the pacemaker circuitry to act, in known manner, as one of the output electrodes of the pacemaker.

Within the embodiment of FIG. 4, it is necessary that at least the cover 17 and the member 23 be of a material which is electrically conductive and body compatible, such as titanium. It is also desirable that the material forming the bottom wall, side walls and flange of the embodiments of FIGS. 1–3 be body compatible, as is well known to the art. However, it has been found that some battery systems are not compatible with titanium. For example, iodine will attack titanium in dry environment. Thus, some lithium-iodine power-source systems are impractical within a titanium canister inasmuch as the lithium will assure a dry environment within the canister cavity 18. It has been found that a stainless steel designated by an American Iron and Steel Institutue (AISI) as No. 304L has the requisite resistance to attack by a lithium-iodine power-source system. Additionally, AISI no. 304L stainless steel has a carbon content low enough to minimize property changes on heating, as occurs when the flange and cover and sealed, and is more resistant to corrosion than would be the case if its carbon content were higher.

Figure 5:
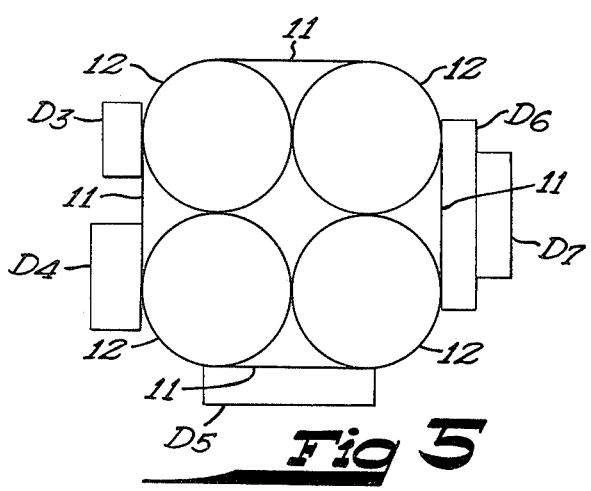
FIG. 5 is a diagrammatic illustration of a portion of a preferred embodiment of the present invention.

Referring now to FIG. 5, there is shown a diagrammatic illustration of the cavity of the power-source canister in either of the embodiments of FIGS. 1–3 and FIG. 4 and the manner in which it accommodates power sources of varying configurations. Also illustrated is the positioning of various pacemaker circuit elements or devices D3-D7 around the periphery of the canister. The devices D3-D7 are typically oscillators, amplifiers, and other electrical components whose use and interconnection in the pacemaker invironment is well known to the prior art. The canister cavity is formed by the straight side wall portions 11 and arcuate portions 12. Each of the straight side wall portions 11 are of approximately equal length and are perpendicular to two of the others and parallel to a third. The arcuate portions are generally circular and have a radius of curvature approximately equal to one-fourth the distance between the parallel ones of the straight side wall portions 11. Thus, the power source canister cavity is a square with rounded corners and can easily accommodate a power source or power sources which are square or rectangular in cross section. In addition, the canister can easily accommodate disc or cylindrically shaped power sources whose radius is equal to or less than the radius of curvature of the arcuate portions 12. For example, FIG. 5 illustrates the placement of four disc or cylindrically shaped power sources within the cavity, the radius of the power sources being equal to the radius of curvature of the arcuate side wall portions 12. From this, it is clear that the power-source canister of the present invention can easily accommodate power sources of varying configurations without alteration of the shape of the canister. In this manner, a pacemaker design can be standarized to physically incorporate the power-source canister of the present invention without regard to the particular power source it contains. The canister can also accommodate some circuit components such as the diode arrangement shown in U.S. Pat. No. 3,757,795 for interconnecting multiple power sources in redundant parallel circuits. Multiple power sources may also be serially connected. Other circuit components, such as the voltage doublers known to the prior art, may also be contained within the canister to raise the voltage level applied to the terminals 16 to enhance the interchangeability of lower voltage power-source arrangements with those having higher voltage level outputs. Thus, the standardized pacemaker design can be easily adapted for use with different power-source systems, and their differing configurations and characteristics, without alteration of the pacemaker design or the configuration of the canister. The desired power-source system is merely selected and a canister containing that system, and any necessary circuit elements, is positioned within the pacemaker unit. In addition, the straight side wall portions 11 provide a convenient surface around which the pacemaker components to be powered can be positioned and preserves more of that space than would be the case if the cannister were generally circular and of a diameter sufficient to accept four of the disc-like power sources as illustrated in FIG. 5.

Many modifications and variations of the present invention are apparent in light of the above teachings. For example, the overall dimension of the straight side wall 11 and the radius of curvature of the arcuate side wall portion 12 may be selected in accordance with the alternative power-source configurations which are desired to be housed therein. It is apparent, however, that the straight side wall portions 11 facilitate the accommodation of power sources having square or rectangular cross sections within the canister cavity while the arcuate side wall portions 12 facilitate the accommodation of power sources having a circular cross section. The straight side wall portions also preserve more space outside the canister for the positioning of pacemaker components than would be the case if the canister side wall were arcuate and dimensioned to accept the alternatively configured power sources. While the power source canister of the present invention has been described within the context of implantable cardiac pacemakers, it is apparent that the teachings contained herein have application in other environments where alternative power-source configurations are to be housed, particularly in other body implantable devices. It is therefore to be understood that while the power source canister of the present invention has unique application within the context of implantable cardiac pacemakers the invention described herein may be practiced other than as specifically described within or without of the pacemaker environment.

What is claimed is:

1. In a power source canister for isolating a power source from the means to be powered when packaged therewith for implantation in a living animal body, and having a bottom wall, a continuous side wall, a cover and feed-through means for allowing an electrical connection between a power source within said canister and the device or devices to be powered, the improvement wherein said bottom wall and side wall define a cavity, said cover being at least coextensive with said cavity, and further comprising flange means extending from said side wall and away from said cavity, said side wall being formed by four generally straight portions of approximately equal length, each straight portion being generally perpendicular to two of the others and generally parallel to a third, and said straight portions being joined by arcuate portions having a radius of curvature approximately equal to one-fourth the distance between said parallel straight portions.

2. The canister of claim 1 wherein said bottom wall, side wall and cover are formed of AISI No. 304L stainless steel.

3. The canister of claim 1 wherein said bottom wall, side wall and cover are formed of AISI No. 304L stainless steel.

4. The canister of claim 1 wherein at least a portion of said flange means and said cover are arcuate in cross section.

5. The canister of claim 1 wherein at least a portion of said flange means and said cover means are flat.

6. The canister of claim 1 wherein said flange means comprises means for allowing said cover to be secured over and close said cavity without encroachment on the volume of said cavity.

7. The canister of claim 6 wherein said means for allowing said cover to be secured over and close said cavity includes means for permitting a heat generating sealing process to seal said cavity at a point spaced therefrom.

8. The canister of claim 7 wherein said bottom wall, side wall and cover are formed of AISI No. 304L stainless steel.

9. The canister of claim 1 wherein said feed-through means extend into said cavity through said side wall.

10. The canister of claim 9 wherein said flange means comprises means for allowing said cover to be secured over and close said cavity without encroachment on the volume of said cavity.

11. The canister of claim 10 wherein said means for allowing said cover to be secured over and close said cavity includes means for permitting a heat generating sealing process to seal said cavity at a point spaced therefrom.

12. The canister of claim 1 wherein said feed-through means comprises at least one terminal means extending through said side wall.

13. The canister of claim 12 wherein there are a plurality of terminal means each extending through said side wall at locations spaced along the perimeter of said side wall.

14. The canister of claim 1 wherein said cover defines at least a portion of the outer surface of the package to be implanted.

15. The canister of claim 14 wherein said bottom wall, side wall and cover are formed of AISI No. 304L stainless steel.

16. In a power source canister for isolating a power source from the means to be powered when packaged therewith for implantation in a living animal body, and having a bottom wall, a continuous side wall, a cover and feed-through means for allowing an electrical connection between a power source within said canister and the device or devices to be powered, the improvement which comprises flange means extending outwardly from said side wall, said feed-through means comprising at least one terminal means extending through said side wall, and said side wall being formed by four generally straight portions of approximately equal length, each straight portion being generally perpendicular to two of the others and generally parallel to a third, and said straight portions being joined by arcuate portions having a radius of curvature approximately equal to one-fourth the distance between said parallel straight portions.

17. The canister of claim 16 wherein there are a plurality of terminal means each extending through said side wall at locations spaced along the perimeter of said side wall each being inclined away from said flange means.

18. The canister of claim 17 wherein said cover is coextensive with said flange means, at least a portion of said flange means and said cover being arcuate in cross section.

19. The canister of claim 17 wherein said cover is coextensive with said flange means, at least a portion of said flange means and said cover being flat.

20. In a power source canister for isolating a power source from the means to be powered when packaged therewith for implantation in a living animal body, and having a bottom wall, a continuous side wall, a cover and feed-through means for allowing an electrical connection between a power source within said canister and the device or devices to be powered, the improvement wherein said side wall is provided with a bevelled portion, said feed-through means including at least one terminal means extending through said bevelled portion, and said side wall being formed by four generally straight portions of approximately equal length, each straight portion being generally perpendicular to two of the others and generally parallel to a third and said straight portions being joined by arcuate portions having a radius of curvature approximately equal to one-fourth the distance between said parallel straight portions.

21. The canister of claim 20 wherein said bottom wall and side wall define a cavity and further comprising means for allowing said cover to be secured over and close said cavity without encroachment on the volume of said cavity.

22. The canister of claim 21 wherein said means for allowing said cover to be secured over and close said cavity includes means for permitting a heat generating sealing process to seal said cavity at a point spaced therefrom.

23. The canister of claim 22 wherein there are a plurality of terminal means each extending through said bevelled portion at locations spaced from each other at locations spaced along the perimeter of said side wall.

24. The canister of claim 20 further comprising flange means extending from said side wall, said bevelled portion extending between said side wall and said flange means, wherein there are a plurality of terminal means each extending through said bevelled portion at locations spaced from each other along the perimeter of said side wall.

25. The canister of claim 24 wherein said cover is coextensive with said flange means.

26. The canister of claim 25 wherein at least a portion of said cover and said flange means are arcuate in cross section.

27. The canister of claim 25 wherein at least a portion of said cover and said flange means are flat.

28. Canister means for isolating a power source from the means to be powered, all the means adapted to be implanted in the body of an animal, comprising:
bottom wall means;
side wall means connected to the bottom wall means and including a portion extending generally perpendicular therefrom to define a cavity and a flange portion extending from said perpendicular portion and surrounding said cavity, the side wall means including four generally straight side means each being generally perpendicular to two other side means and generally parallel to a third side means, and four arcuate corner means each connected between two straight side means to form four arcuate corners of the side wall means, the corner means having a predetermined radius of curvature; and
cover means for connection to the side wall means flange portion for sealing the cavity at a point spaced from said cavity.

29. The canister of claim 28 wherein the straight side means are of approximately equal length, the radius of curvature of said corner means being approximately equal to one-fourth the distance between said parallel straight side means.

30. The canister of claim 29 further comprising a plurality of terminal means extending through said side wall means at locations spaced along the perimeter of said side wall means.

31. The canister of claim 30 wherein said side wall means includes a bevelled portion, said terminal means extending through said side wall means bevelled portion.

32. The canister of claim 31 wherein said cover means includes electrode means for making electrical contact with said animal body.

33. The canister of claim 32 wherein said bottom wall means, side wall means and cover means are formed of AISI No. 304L stainless steel.

34. The canister of claim 28 wherein said bottom wall means, side wall means and cover means are formed of AISI No. 304L stainless steel.

35. The canister of claim 28 further comprising a plurality of terminal means extending through said side wall means at locations spaced along the perimeter of said side wall means.

36. The canister of claim 35 wherein said side wall means includes a bevelled portion, said terminal means extending through said side wall means bevelled portion.

37. The canister of claim 28 further comprising at least one terminal means extending through said side wall means.

* * * * *

UNITED STATES PATENT AND TRADEMARK OFFICE
CERTIFICATE OF CORRECTION

PATENT NO. : 3,957,056
DATED : May 18, 1976
INVENTOR(S) : Richard H. Comben and Richard L. Doty It is certified that error appears in the above-identified patent and that said Letters Patent are hereby corrected as shown below:

Column 1, line 63, "layer" should be -- larger --.

Column 5, line 44, "and sealed" should be -- are sealed --.

Delete claim 3 and insert:

-- 3. The canister of claim 1 wherein said bottom wall, side wall and cover are formed of titanium. --.

Signed and Sealed this

Nineteenth Day of October 1976

[SEAL]

Attest:

RUTH C. MASON
Attesting Officer

C. MARSHALL DANN
Commissioner of Patents and Trademarks